United States Patent [19]

Larson

[11] Patent Number: 5,602,899
[45] Date of Patent: Feb. 11, 1997

[54] ANODE ASSEMBLY FOR GENERATING X-RAYS AND INSTRUMENT WITH SUCH ANODE ASSEMBLY

[75] Inventor: Paul E. Larson, Bloomington, Minn.

[73] Assignee: Physical Electronics Inc., Eden Prairie, Minn.

[21] Appl. No.: 593,308

[22] Filed: Jan. 31, 1996

[51] Int. Cl.$^6$ ................................................. H01J 35/12
[52] U.S. Cl. ............................................................ 378/143
[58] Field of Search ..................................... 378/119, 143

[56] References Cited

U.S. PATENT DOCUMENTS

| | | | |
|---|---|---|---|
| 3,766,381 | 10/1973 | Watson | 250/49.5 AE |
| 3,992,633 | 11/1976 | Braun et al. | 378/2 |
| 4,972,449 | 11/1990 | Upahdya et al. | 378/144 |
| 5,148,462 | 9/1992 | Spitsyn et al. | 378/143 |
| 5,315,113 | 5/1994 | Larson et al. | 250/305 |

OTHER PUBLICATIONS

"Diamond Takes the Heat" by T. J. Moravec et al. Advanced Packaging 8–11 (Oct. 1993).

*Primary Examiner*—David P. Porta
*Assistant Examiner*—David Vernon Bruce
*Attorney, Agent, or Firm*—H. S. Ingham

[57] ABSTRACT

An anode assembly for generating x-rays has a mounting block with a channel therethrough, with a diamond wafer mounted sealingly across an opening in the block so as to have an inner surface in contact with the coolant flowing in the channel. Alternatively, a thicker diamond member is mounted in the block with thermal conduction through the metal block. A metal anode film bonded to the outer surface of the diamond is receptive of a focused electron beam to generate x-rays. The diamond provides cooling in compensation for the film being heated by the electron beam. The assembly is useful in a scanning x-ray monochromator instrument for chemical analysis of a specimen surface.

22 Claims, 4 Drawing Sheets

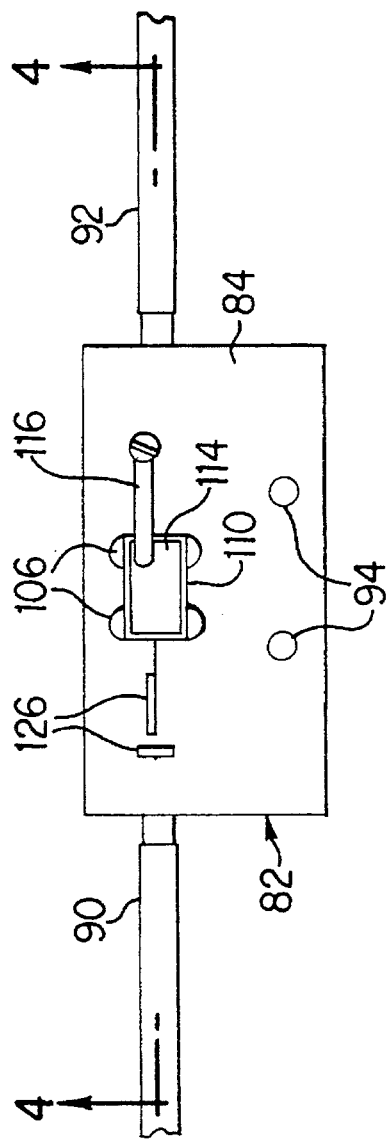
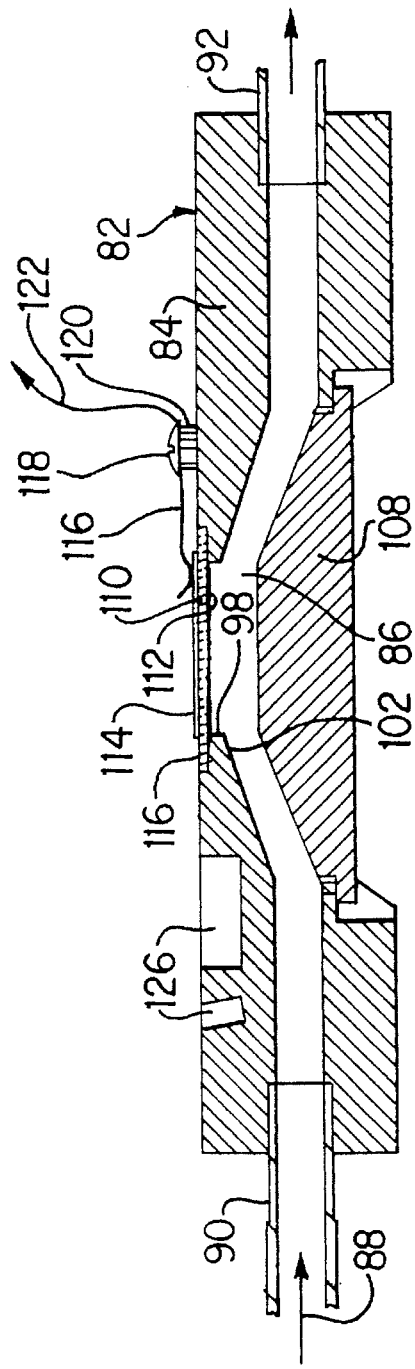

ANODE ASSEMBLY FOR GENERATING X-RAYS AND INSTRUMENT WITH SUCH ANODE ASSEMBLY

This invention relates to generation of x-rays, and particularly to an anode assembly for generating x-rays, and to instruments incorporating such an anode assembly.

BACKGROUND

Several types of surface analysis instruments utilizing x-rays have evolved in recent years. One approach to chemometric surface analysis is electron spectroscopy for chemical analysis (ESCA), also known as x-ray photoelectron spectrometry (XPS), which involves irradiating a sample surface with x-rays and detecting the photoelectrons emitted. The photoelectron energies are characteristic of chemical elements in the surface, and are filtered by an electrostatic or magnetic analyzer which allow only electrons of a specified narrow energy band to pass through to a detector. The intensity of the detected beam typically represents the concentration of a given chemical constituent on or near a specimen surface. U.S. Pat. No. 3,766,381 (Watson) describes such a system that utilizes a hemispherical electrostatic analyzer that transmits electrons of selected energy to a detector. By selecting a range of energies transmitted, analyzing of the electron energies is effected.

A recent development is scanning x-ray photoelectron spectroscopy as disclosed in U.S. Pat. No. 5,315,113 (Larson et al). In this instrument an electron beam is focused on an anode causing emission of x-rays from the irradiated spot. The x-rays are focused by a component such as a concave Bragg crystal monochromator onto the surface of a sample specimen to be chemically analyzed. The monochromator forms an x-ray image of the anode spot on a small pixel area on the surface of the specimen. When the electron beam steps laterally, the x-ray spot on the specimen steps correspondingly from one pixel to the next. The emitted photoelectrons are energy analyzed at each pixel so that a map of the surface chemistry can be constructed. A particular pixel area may be selected for analysis, or the electron beam may be rastered so that the x-ray spot also is rastered for mapping.

The anode for an ESCA instrument typically is magnesium or, particularly in an instrument with a monochromator, aluminum for its K$\alpha$ x-ray line. Other metals such a tungsten are used for x-ray emissions in other applications. High power is desirable in the electron beam to produce the greatest intensity of x-radiation and thereby attain maximum sensitivity. However, nearly all the power is converted into heat in the anode and can cause melting, diffusion or other deterioration which shortens the useful life of the anode. The normal operating power thus is a compromise between beam intensity and anode lifetime. For this reason, the anode should conduct heat away efficiently. For optimum cooling the anode material is in the form of a thin film of a few microns. In the case of ESCA instruments, substrates for the aluminum or magnesium film typically are water cooled silver or copper, but beam power is still limited. A further problem with a support of silver and copper is erosion of these softer metals by cooling water.

An object of the invention is to provide a novel anode assembly for an x-ray instrument. A particular object is to provide such an anode assembly that is receptive of a focused electron beam to effect x-rays from an anode spot. Another object is to provide such an anode assembly capable of improved life and/or increased x-ray intensity from an anode spot. A further object is to provide an improved apparatus incorporating such an anode assembly for generating x-rays. Yet another object is to provide such an apparatus in the form of an x-ray photoelectron spectrometer for chemical analysis of small areas of a specimen surface.

SUMMARY

The foregoing and other objects are achieved, at least in part, by an anode assembly for generating x-rays, comprising a support block having a channel therein receptive of a fluid coolant, a diamond member mounted in the block so as to have an outer surface diamond member facing outwardly, and a metal anode film bonded to the outer surface. The diamond member communicates thermally with the coolant. The anode film is receptive of an impinging electron beam to generate x-rays characteristic of the metal. The diamond member thereby provides cooling in compensation for the anode member being heated by the electron beam.

In a preferred embodiment, the support block is in the form of a housing having an opening from the channel, and the diamond member is mounted sealingly to the housing across the opening so as to have an inner surface in contact with the coolant. More preferably, the housing is formed of a material such as molybdenum having a low thermal expansion coefficient, and the diamond member is in the form of a wafer sealed across the opening. In another embodiment, the support block is formed of silver or copper, the diamond is a thicker member such as a cube affixed in an opening in the block, and thermal communication of the diamond member with the coolant is through a portion of the support block.

The anode assembly is incorporated advantageously into an apparatus in which the anode film is receptive of an electron beam so as to generate the x-rays, and a means is receptive of the x-rays for utilizing the x-rays. A particular apparatus is an otherwise conventional x-ray microprobe instrument with a focusing means such as monochromator for focusing the x-rays to a specimen surface, and an photoelectron energy analyzer for chemometric analysis of the surface. In such case, an electron gun produces a focused electron beam so as to generate the x-rays from an anode spot on the anode film. The electron beam is positioned to selectively position an anode spot over the film.

BRIEF DESCRIPTION OF THE DRAWINGS

FIG. 3 is a top view of an assembly of an anode assembly incorporated into the instrument of FIG. 1.

FIG. 4 is a longitudinal section taken at 4—4 of FIG. 3.

DETAILED DESCRIPTION

Figure 1:
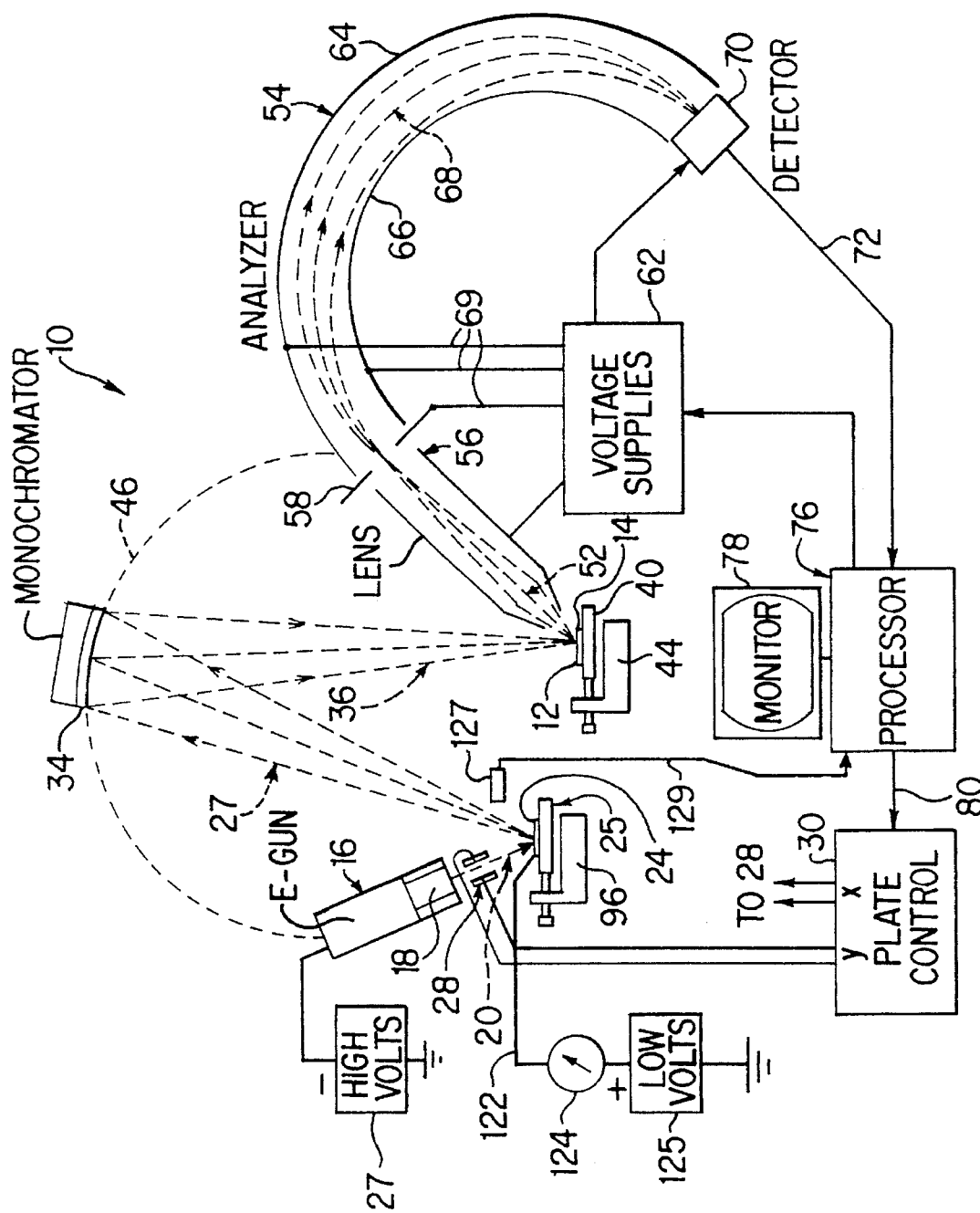
FIG. 1 is a schematic diagram of an instrument incorporating the invention.

A preferred utilization of the invention, illustrated schematically in FIG. 1, is in a scanning x-ray monochromator instrument 10 for analysis of a sample specimen 12 of the type disclosed in the aforementioned U.S. Pat. No. 5,315,113 incorporated herein by reference. Such an instrument is sold by Physical Electronics Inc. under the trademark QUANTUM 2000. An electron gun 16 has an appropriate electron lens system 18 for focusing an electron beam 20 an anode 24 of an anode assembly 25. The assembly may be mounted on a movable stage 96 for positioning the anode transversely. The gun may be conventional, for example as described in the aforementioned patent. The electron beam is focused to a spot 26 (FIG. 2) on the anode surface, typically from about 5 to 200 μm diameter. This results in the generation of x-rays 27 from the anode, and in particular from the anode spot.

In an instrument with a monochromator, the anode 24 advantageously is formed of aluminum in to provide a desired x-ray emission energy band aluminum K-alpha compatible with the monochromator. More generally the metal may be any metal such as magnesium in other ESCA instruments, or tungsten, or as otherwise desired for an anode for generating x-rays. Through a voltage supply 27, the anode is positive with respect to the gun cathode, generally 1500 volts to 30 kV, and more typically 10 KV to 20 KV to provide electron energy to generate the x-rays. The anode in the present example is at or near ground potential, but may be at another potential, for example with the electron gun grounded.

Figure 2:
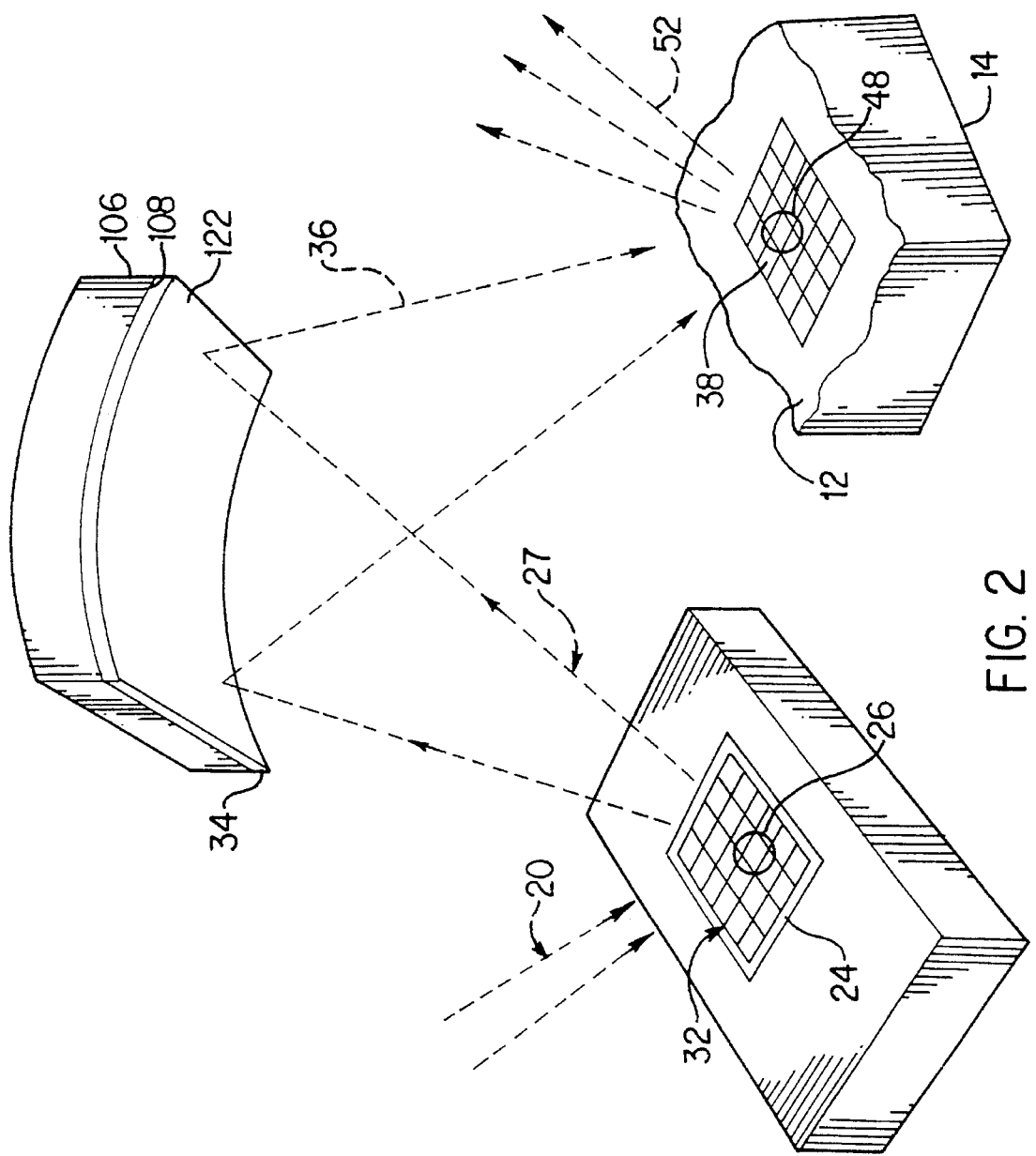
FIG. 2 is a detail in perspective of an anode, a specimen and a monochromator in the instrument of FIG. 1.

Deflection plates 28 (one pair shown in FIG. 1) direct the electron beam 20 from the electron gun 16 to the anode spot 26 among an array of such locations 32 on the anode surface (FIG. 2). Voltages from a deflection control 30, which is controlled by a processor 76 via line 80, are applied to the deflector plates arranged in both x and y axes to deflect the beam. The control 30 positions or rasters the focused electron beam 20 across the anode surface, and the x-rays are emitted from the anode at the anode spot.

The x-rays may be utilized in any manner desired. In the preferred instrument, at least a portion of the x-rays are focused to the sample specimen, advantageously by a Bragg crystal monochromator 34 as disclosed the aforementioned U.S. Pat. No. 5,315,113. Such a crystal is curved and is based on the geometry of a conventional Rowland circle 46, in which the center of the anode 24, the crystal 34 and the center of the sample surface 12 are substantially on the circle. The focusing of the x-rays 36 effects an x-ray spot 38 coinciding with a pixel area 48 on the specimen surface, the x-ray spot being an x-ray image of the anode spot 26. The x-ray spot may be stationary at a selected pixel area by adjustment of the voltages on the deflection plates, or scanned with the rastering of the electron beam.

The x-rays cause photoelectrons 52 to be emitted from the scanning pixel area 48 of the specimen, with electron energies associated with chemical species in the specimen. Scanning speed may be between zero (for a selected spot) and 100 m/sec, e.g. 10 m/sec. The energies are analyzed by an appropriate device such as a hemispherical analyzer 54 receives at least a portion of the electrons 52 via a conventional electron lens 56 which focuses the electrons into the analyzer entrance 58. With selected voltage from a voltage source 62 applied via lines 69 across the hemispheres 64, 66 of the analyzer, electrons of selected energy travel in a range of trajectories 68 so as to exit the analyzer onto a detector 70. The latter may be a conventional multichannel detector. Other analyzing systems and/or detectors may be used, for example a coaxial cylindrical analyzer of electron energy such as taught in U.S. Pat. No. 4,048,498 (Gerlach et al). A magnetic analyzer also may be used.

Signals from the detector 70, corresponding to the number and energy of electrons detected, are carried on a line 72 (via an appropriate amplifier, not shown) a processing unit 76 which combines control electronics and computer processing. This converts the spectral data to information on chemical species that are present in the specimen pixel area 48 (FIG. 2). The information is stored and displayed on a monitor 78 and/or printed. By cooperating the display means (including the processor) with the analyzer voltages and the electron rastering means 28, 30, a mapping of chemical species over specimen surface can be effected and displayed.

In the anode assembly 25 (FIGS. 3, 4) according to the present invention, a mounting block in the form of a housing 82 has a mounting wall 84 formed of a material having a low thermal expansion coefficient. Molybdenum metal is especially suitable for the housing. A ceramic such as a machinable alumina-based ceramic may be used, but would have to be metallized to prevent charge buildup. For reasons explained below, the housing is advantageously formed of a refractory metal, i.e. tungsten, molybdenum, tantalum or columbium. Although the material for the mounting wall is not necessarily the same as the rest of the housing, preferably substantially the entire housing is formed from the same material, viz. molybdenum. The housing has a channel 86 therein receptive of a fluid coolant 88, with a fluid inlet 90 and a fluid outlet 92.

Holes 94 through the housing next to the channel provide for mounting to a movable stage 96 (FIG. 1). The mounting wall has a rectangular opening 98 therein connecting to the channel, with a ledge 102 surrounding the opening. The ledge may be formed by a thinner ring of wall (as shown) to place the wafer closer to the flowing fluid, or simply may be the edge of the wall at the same thickness. The opening and ledge may be formed in part by milling slots 106 in the wall. The channel is formed conveniently in a block portion of the housing (that includes the mounting wall), with a bottom cover 108 brazed in place to complete the channel enclosure. As the anode operates in a vacuum, all brazing associated with the housing must be vacuum tight. Gaskets and fasteners such as screws may be used in place of brazing.

A diamond wafer 110 is affixed sealingly to the ledge 102 so as to cover the opening 98. The wafer is commercially available as chemical vapor deposited (CVD) or arc plasma formed diamond. The wafer should be thick enough to provide support but otherwise is as thin as practical, generally between about 0.1 mm and 1 mm, for example 0.5 mm thick by 6 mm by 10 mm. Diamond quality should be such as to provide high thermal conductivity. Although single crystal would be ideal, available material of sufficient size is polycrystalline with a columnar structure directionally normal to the large surfaces. Isotropically pure diamond, particularly substantially all carbon twelve ($C^{12}$), is preferable but expensive. Suitable diamond wafers are available from several sources: GE Superabrasives, Worthington, Ohio; Dubbeldee Harris Diamond Corp., Mount Arlington, N.J.; and Norton Diamond Film, Northboro, Mass. The diamond may be affixed to the molybdenum by brazing with 82–18 gold-nickel alloy AMS-4787 which is available, for example, under the tradename NIORO™ from Wesgo Co. A braze about 25 to 50 μm thick is suitable. A material having a low thermal expansion coefficient is desired for at least the mounting wall 84 of the housing, as the diamond has a low expansion coefficient, to overcome potential problems with shear stress upon cooling after brazing of the diamond to the housing. The coefficient should be less than about 12 ppm/° C., e.g. 6 ppm/° C. for molybdenum. The refractory metals are generally in this category.

The inner surface 112 of the diamond wafer is in contact with the coolant. The channel 86 in the housing should be configured to effect channelling of the fluid at a high velocity across this inner surface to cool the diamond, typically about 5 m/sec across the inner surface. Coolant flow rate is preferably such as to allow boiling (for optimum heat absorbance) while sweeping away the bubbles. If better cooling is desired or necessary, conventional refrigerant or liquid nitrogen may be used; however, supercooling may condense contaminants on the anode surface.

A metal film 114 is bonded to the outer surface 116 of the diamond wafer 110 to provide the anode that is receptive of the impinging electron beam to generate x-rays. It is preferable for the diamond surface 116 under the film to be polished. The film is produced by a conventional or other desired method such as sputtering or CVD metallization. The anode metal for the film is selected according to the instrument, for example magnesium or preferably aluminum as described above. The film should be as thin as possible for heat transfer, but thick enough so that most of the beam energy is dissipated in the film, not in the diamond. Beam penetration for aluminum is about 0.6 μm for 10 keV electrons and 2.4 μm for 20 keV. To minimize wasted energy, the film thickness should be about twice the penetration depth. Thus a suitable film thickness for the latter beam is about 4 μm. There is a blooming of about 1 μm diameter from a 10–20 keV beam into the film, providing a limit of resolution and, therefore, a minimum practical beam diameter of 1 μm for the film for this beam energy range. For the other dimensions, the diamond wafer and anode film may have an area several times the anode area used, so that the area in use can be shifted by the stage 96 when the original area becomes deteriorated.

Significant local heating results from the incident electron beam, requiring a limit on beam power to avoid damaging or rapidly deteriorating the anode film. The diamond in the present case has a high thermal conductivity to draw heat from the film to the coolant, in compensation for the film being heated by the electron beam, particularly at the anode spot. It was determined that an electron beam power of 0.4 watts per micrometer of beam diameter can be achieved, which is double that for the prior configuration with silver or copper substrate for the aluminum film.

With prior systems, the beam current may be measured by electrically floating the anode and its support system, but this is difficult and inaccurate, particularly with cooling water. The current is more readily measured with a structure of the present invention.

For measuring current, a means for electrically contacting the anode film is formed, for example, by a spring contact 116 (FIGS. 3, 4) mounted on and electrically insulated from the molybdenum housing cover by a machine screw 118 held in insulating bushings 120. One end of the contact is urged against the anode film. An electrical lead 122 connects from the spring contact at the screw to the positive terminal of a low voltage supply 125, typically 50–100 volts (e.g. 90 volts), through an ammeter 124 for measuring the anode current. The low voltage supply is not essential but permits more accurate current measurement by collecting low energy secondary electrons which would otherwise escape from the anode. Because the anode is relatively small and electrically well insulated by the diamond border, the current measurement is simple and free of leakage currents which could cause errors. If it is not necessary or desired to measure the anode current directly, the anode may be grounded by extending the anode film to the edges of the diamond so that it contacts the grounded housing. The electron gun cathode is connected to the negative side of the high voltage power supply 27 and the electrons strike the anode with an energy which is directly proportional to the potential difference between the cathode and the anode. Beam power is the product of this potential difference and the beam current.

One or preferably a pair of orthogonal slots 126 (or single edges) in the mounting wall adjacent to the anode surface is used conventionally for determination of electron beam width. The beam is traversed across an edge of a slot (or single edge) and secondary current is collected by an electrode 127 mounted above the anode. This current may be monitored, for example, as a pattern on an oscilloscope where it is seen to change from one level to another during the traverse, the width of the pattern in the change representing the beam width. Advantageously, as shown, the electrode signal is directed on a lead 129 to the computer 76 where it is digitized. With further input of the plate control signals, the beam width is computed and displayed.

With prior housings of silver and copper, there has been melting at the edges of the slot 126 by the beam. The use of a refractory metal such as molybdenum resists this type of deterioration. If such metal is used, it is only necessary for the mounting wall 84 to be molybdenum, with the rest of the housing being another desired material such as stainless steel. However, a full housing of refractory metal has been found to be practical.

Although the foregoing is directed to an instrument having a concentrated electron beam for effecting x-rays focussed with a monochromator, there are other applications. For example an ESCA instrument such as described in the aforementioned U.S. Pat. No. 3,766,381 is used to provide energy analysis of photoelectrons emitted from a solid surface as a result of x-ray excitation, where there is no scanning. In such an instrument, magnesium as an alternative to aluminum may be used for the anode. As there is no focused electron beam or anode spot, there is no concentrated heating as in the scanning x-ray instrument. Nevertheless, high power flow of electrons to the anode may result in excessive heating where an anode assembly could be incorporated, and the present anode assembly allows the electron beam power to be increased further. Other metals such as tungsten may be desirable for the anode.

Figure 5:
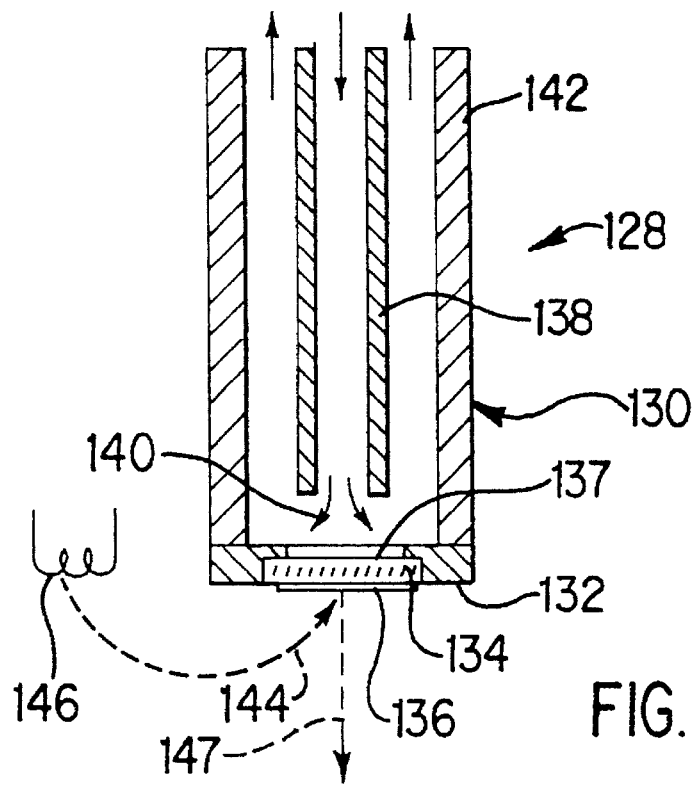
FIG. 5 is a longitudinal section of another embodiment of an anode assembly of the invention.

In an embodiment of an anode assembly 128 for ESCA (FIG. 5), the assembly has a modified configuration. In this case the housing 130 is cylindrical with the mounting wall 132 sealed across the end of the cylinder. The diamond wafer 134 with the anode film 136 is affixed centrally over an opening in the end wall 132. An axial tube 138 in the housing directs coolant 140 against the diamond, and the coolant flows out between the tube and the housing cylinder 142. The electron beam 144 is provided by a heated filament 146 that is located to one side so as to be out of the path of emitted photoelectrons 147. The film is anodic with respect to the filament.

Figure 6:
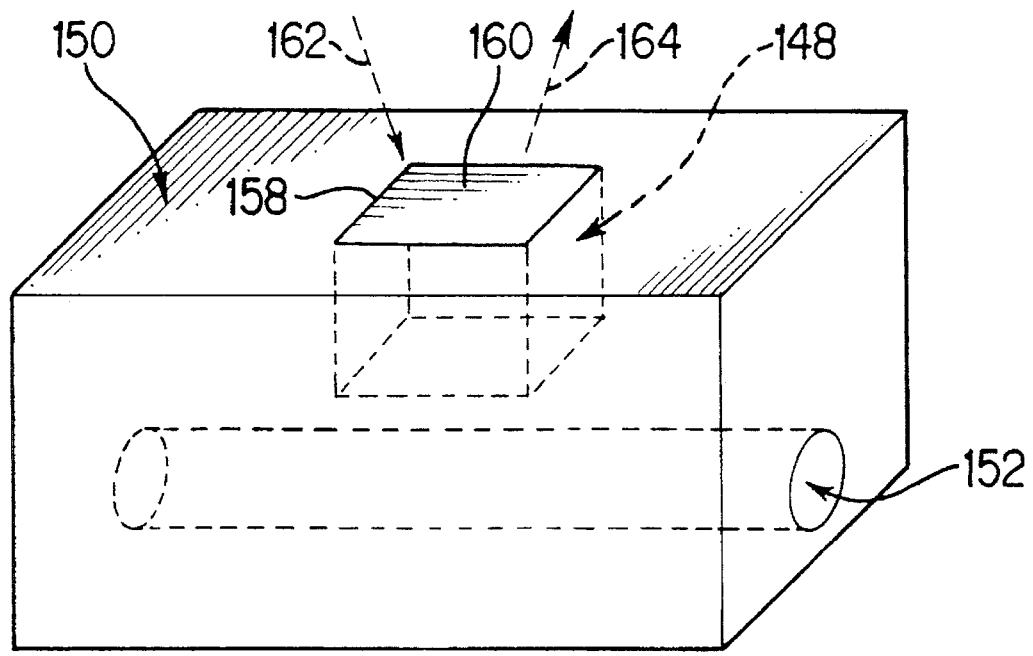
FIG. 6 is a semi-transparent perspective of a further embodiment of an anode assembly of the invention.

In a further embodiment (FIG. 6) for producing x-rays, the diamond is in the form of a thicker member 148, for example cubic or gem-shaped. The diamond is affixed in an opening corresponding to the shape of the diamond in a mounting block 150 which has a channel 152 therethrough for fluid coolant. The cubic diamond has its five inner surfaces brazed in thermal contact with the block so as to communicate thermally with the flowing coolant through the block. (In an alternative arrangement, not shown, at least some of the diamond surfaces may contact the coolant.) An outer surface 158 of the diamond faces oppositely (outwardly). The anode film 160 is bonded to the outer surface. The anode film is again receptive of an impinging electron beam 162 to generate x-rays 164 characteristic of the metal, and the diamond member provides cooling in compensation for the anode film being heated by the electron beam. In this configuration, the several sides of the diamond member help to further dissipate the heat. In this embodiment without direct cooling of the diamond, a high conductivity metal such as silver or copper is preferable for the housing.

An anode assembly according to the invention has a number of benefits: The improved cooling of the anode allows higher electron beam power for higher sensitivity, or longer anode life with prior current levels, or both improved sensitivity and longer life at intermediate power levels. The hard diamond resists erosion that previously limited the life of housings made of silver or copper, or required lower power levels. The electrically insulating diamond substrate for the anode allows convenient, accurate monitoring of the electron beam current. The diamond substrate is substantially immune to damage from the heating, whereas silver and copper deteriorated, particularly from interfacial diffusion. Beam size can be measured more effectively on the refractory metal housing without damaging the slot edges used for the measurement.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. An anode assembly for generating x-rays, comprising:
   a housing having a channel therein receptive of a fluid coolant, the housing further having an opening from the channel and comprising a mounting wall formed of a refractory metal with a low thermal expansion coefficient;
   a diamond wafer mounted sealingly to the mounting wall across the opening so that an outer surface of the diamond wafer faces outwardly and an inner surface of the diamond wafer is in contact with the coolant; and
   a metal anode film bonded to the outer surface, the anode film being receptive of an impinging electron beam to generate x-rays characteristic of the metal, whereby the diamond wafer provides cooling in compensation for the anode member being heated by the electron beam, and wherein the mounting wall has one slot or a pair of orthogonal slots therein for traversing the electron beam to determine width of the electron beam.

2. The assembly of claim 1 further comprising contact means for electrically contacting the anode film.

3. The assembly of claim 1 wherein the support block if formed of silver or cooper, and thermal communication of the diamond member with the coolant is through a portion of the support block.

4. The assembly of claim 1 wherein the refractory metal is molybdenum.

5. The assembly of claim 4 wherein the housing is formed of molybdenum.

6. The assembly of claim 1 wherein the anode film is aluminum or magnesium.

7. The assembly of claim 6 wherein the anode film is aluminum.

8. An instrument for analysis of a specimen surface by generation of x-rays, comprising electron means for producing an electron beam, an anode assembly with a metal anode film disposed to receive the electron beam so as to generate x-rays from the anode film, and utilization means receptive of the x-rays for utilizing the x-rays, wherein the anode assembly comprises a support block having a channel therein receptive of a fluid coolant, a diamond member mounted in the block so as to have an outer surface diamond member facing outwardly, and a metal anode film bonded to the outer surface, the diamond member communicating thermally with the coolant, and the anode film being receptive of an impinging electron beam to generate x-rays characteristic of the metal, whereby the diamond member provides cooling in compensation for the anode member being heated by the electron beam;
   wherein the electron means comprises an electron gun for producing a focused electron beam so as to generate the x-rays from an anode spot on the anode film, and the utilization means comprises focusing means receptive of at least a portion of the x-rays for focusing said portion of x-rays on an analysis area on the specimen surface such that photoelectrons are emitted from the analysis area with electron energies characteristic of chemical species at the analysis area, analyzer means receptive of at least a portion of the photoelectrons for analyzing the electron energies, and processing means cooperative with the analyzer means for generating specimen information representative of the electron energies and thereby chemical species of the specimen surface.

9. The instrument of claim 8 further comprising contact means for electrically contacting the anode film, and current measuring means connected between the contact means and the electron means to measure electron beam current to the anode film.

10. The instrument of claim 8 wherein the support block is formed of silver or copper, and thermal communication of the diamond member with the coolant is through a portion of the supporting block.

11. The instrument of claim 8 wherein the support block is in the form of a molybdenum housing having an opening from the channel, the diamond member is in the form of a diamond wafer mounted sealingly to the housing across the opening so as to have an inner surface in contact with the coolant, and the anode film is aluminum.

12. The instrument of claim 8 wherein the support block is formed of silver or copper, and thermal communication of the diamond member with the coolant is through a portion of the support block.

13. The instrument of claim 8 wherein the focusing means comprises a concave Bragg crystal monochromator.

14. The instrument of claim 8 wherein the electron means further comprises positioning means for positioning the electron beam on the anode film so as to selectively position the anode spot on the anode film, whereby the analysis area is correspondingly positioned on the specimen surface.

15. The instrument 8 wherein the mounting wall is formed of a refractory metal.

16. The instrument of claim 15 wherein the mounting wall has one slot or a pair of orthogonal slots therein for traversing the electron beam to determine width of the electron beam.

17. The instrument of claim 15 wherein the refractory metal is molybdenum.

18. The instrument of claim 17 wherein the housing is formed of molybdenum.

19. The instrument of claim 8 wherein the anode film is aluminum or magnesium.

20. The instrument of claim 19 wherein the anode film is aluminum.

21. The instrument of claim 8 wherein the support block is in the form of a housing having an opening from the channel, and the diamond member is mounted sealingly to the housing across the opening so as to have an inner surface in contact with the coolant.

22. The instrument of claim 21 wherein the housing comprises a mounting wall formed of a material having a low thermal expansion coefficient, the mounting wall has therein the opening from the channel, and the diamond member is in the form of a diamond wafer mounted sealingly to the mounting wall across the opening.

* * * * *